United States Patent
Pretz et al.

(10) Patent No.: US 9,834,496 B2
(45) Date of Patent: Dec. 5, 2017

(54) REACTIVATING PROPANE DEHYDROGENATION CATALYST

(75) Inventors: Matthew Pretz, Lake Jackson, TX (US); Lin Luo, Sugar Land, TX (US); Susan Domke, Midlothian, VA (US); Howard W. Clark, Lake Jackson, TX (US); Richard A. Pierce, Lake Jackson, TX (US); Andrzej M. Malek, Midland, MI (US); Mark W. Stewart, Pearland, TX (US); Brien A. Stears, League City, TX (US); Albert E. Schweizer, Jr., Port St. Lucie, FL (US); Guido Capone, San Giuliano Milanese (IT); Duncan P. Coffey, Lake Jackson, TX (US); Isa K. Mbaraka, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 606 days.

(21) Appl. No.: 14/122,201

(22) PCT Filed: Jul. 11, 2012

(86) PCT No.: PCT/US2012/046188
§ 371 (c)(1),
(2), (4) Date: Nov. 25, 2013

(87) PCT Pub. No.: WO2013/009820
PCT Pub. Date: Jan. 17, 2013

(65) Prior Publication Data
US 2014/0200385 A1    Jul. 17, 2014

Related U.S. Application Data

(60) Provisional application No. 61/507,227, filed on Jul. 13, 2011.

(51) Int. Cl.
| | | |
|---|---|---|
| C07C 5/333 | (2006.01) | |
| B01J 23/62 | (2006.01) | |
| B01J 23/96 | (2006.01) | |
| B01J 38/02 | (2006.01) | |
| B01J 38/12 | (2006.01) | |
| B01J 38/14 | (2006.01) | |
| C07C 5/32 | (2006.01) | |

(52) U.S. Cl.
CPC ............ *C07C 5/3337* (2013.01); *B01J 23/62* (2013.01); *B01J 23/96* (2013.01); *B01J 38/02* (2013.01); *B01J 38/12* (2013.01); *B01J 38/14* (2013.01); *C07C 5/325* (2013.01); *B01J 2523/00* (2013.01); *C07C 2521/12* (2013.01); *C07C 2523/04* (2013.01); *C07C 2523/08* (2013.01); *C07C 2523/14* (2013.01); *C07C 2523/42* (2013.01); *C07C 2523/44* (2013.01); *C07C 2523/46* (2013.01); *C07C 2523/62* (2013.01); *C07C 2527/224* (2013.01); *Y02P 20/52* (2015.11); *Y02P 20/584* (2015.11)

(58) Field of Classification Search
CPC .......... C07C 5/32–5/367; B01J 23/38–23/628
USPC ................................ 585/616, 440, 654–663
See application file for complete search history.

(56) References Cited

U.S. PATENT DOCUMENTS

| | | | | |
|---|---|---|---|---|
| 6,916,756 B2 * | 7/2005 | Schindler | ................. | B01J 23/90 502/38 |
| 2002/0198428 A1 * | 12/2002 | Iezzi | ...................... | B01J 8/0055 585/654 |
| 2004/0242945 A1 * | 12/2004 | Pelati | ....................... | B01J 23/08 585/444 |
| 2004/0259727 A1 * | 12/2004 | Bartolini | .................. | B01J 23/34 502/324 |
| 2005/0177016 A1 * | 8/2005 | Sanfilippo | .............. | B01J 8/0055 585/444 |
| 2008/0194891 A1 * | 8/2008 | Pretz | ..................... | C07C 5/3332 585/252 |
| 2008/0249342 A1 * | 10/2008 | Iaccino | .................... | B01J 29/48 585/402 |
| 2010/0236985 A1 * | 9/2010 | Luo | ........................... | B01J 23/62 208/138 |
| 2012/0083637 A1 * | 4/2012 | Clem | ....................... | B01J 29/48 585/415 |
| 2014/0142362 A1 * | 5/2014 | Davydov | ................ | C07C 5/327 585/659 |
| 2014/0378731 A1 * | 12/2014 | Iezzi | ....................... | B01J 21/12 585/660 |

\* cited by examiner

*Primary Examiner* — In Suk Bullock
*Assistant Examiner* — Ali Z Fadhel
(74) *Attorney, Agent, or Firm* — Dinsmore & Shohl LLP

(57) ABSTRACT

Increase propane dehydrogenation activity of a partially deactivated dehydrogenation catalyst by heating the partially deactivated catalyst to a temperature of at least 660° C., conditioning the heated catalyst in an oxygen-containing atmosphere and, optionally, stripping molecular oxygen from the conditioned catalyst.

8 Claims, No Drawings

REACTIVATING PROPANE DEHYDROGENATION CATALYST

This application is a non-provisional application claiming priority from the U.S. Provisional Patent Application No. 61/507,227, filed on Jul. 13, 2011, entitled "REACTIVATING PROPANE DEHYDROGENATION CATALYST" the teachings of which are incorporated by reference herein, as if reproduced in full hereinbelow.

This invention relates generally to a process for at least partially restoring alkane dehydrogenation activity, especially propane dehydrogenation (PDH) activity, of a partially deactivated dehydrogenation catalyst. This invention relates more particularly to such a process that yields a reactivated dehydrogenation catalyst, especially a PDH catalyst, with a dehydrogenation activity, particularly a PDH activity, greater than that obtained by subjecting the partially deactivated dehydrogenation catalyst only to coke removal.

Conventional catalyst reactivation or regeneration processes that treat catalysts with a reduced catalytic activity due, at least in part, to deposition of coke on catalyst surfaces involve removal of that coke, generally by contacting such catalysts with high temperature (e.g. at least ($\geq$) 450 degrees Celsius (° C.) for an ethanol dehydrogenation catalyst and $\geq$650 ° C. for a fluid catalyst cracking (FCC) catalyst)) air or another oxygen-containing gas. The conventional catalyst reactivation processes do not, however, fully restore or even substantially fully restore catalytic activity of noble metal-containing (e.g. Pt-containing) dehydrogenation catalysts to a level equaling or even approaching that of fresh, unused dehydrogenation catalysts. Those who practice alkane dehydrogenation, especially PDH, understand that as activity of a catalyst decreases, alkene production also decreases to a point where process economics dictate replacement of the deactivated catalyst with fresh catalyst. Such practitioners desire an increase in activity of a regenerated catalyst, preferably an increase in conjunction with a delay in needing to introduce fresh catalyst.

A typical regeneration of a Pt-based dehydrogenation catalyst involves many steps: coke combustion, drying and Pt-redispersion and reduction. See e.g. U.S. Pat. No. 3,652,231 (Greenwood et al.), U.S. Pat. No. 3,986,982 (Crowson et al.), and U.S. Pat. No. 5,457,077 (Williamson et al.).

U.S. Pat. No. 5,457,077 provides a regeneration process for reconditioning catalyst particles containing Pt by transferring the catalyst particles through a combustion zone and a reconditioning zone. The reconditioning zone simultaneously effects drying of catalyst particles and redispersion of Pt with a heated gas stream that contains chlorine and oxygen.

U.S. Pat. No. 3,986,982 relates to chlorine regeneration of platinum group metal (e.g. Pt, palladium (Pd), rhodium (Rh), ruthenium (Ru), osmium (Os) and iridium (Ir)) zeolite catalysts by a) a burn off of deposits on the catalyst at no more than 500 ° C., b) treatment with inert gas, 0.5 volume percent (vol %) to 20 vol % oxygen and 5 parts by volume per million parts by volume (ppv) to 500 ppv chlorine at 400° C. to 550° C., c) a purge to remove residual oxygen and chlorine, and d) reduction in a stream of hydrogen gas at 200° C. to 600° C.

U.S. Pat. No. 2,773,014 (Snuggs et al.) discloses hydrocarbon reforming with a platinum catalyst and a regeneration system for the catalyst. Regeneration involves bringing catalyst contained in a fixed reactor bed to an elevated temperature of about 850 degrees Fahrenheit (° F.) (454° C.) and burning off carbonaceous deposits (otherwise known as "coke") on the catalyst in the presence of a small amount of air. Subsequent to regeneration, Snuggs et al. effects a rejuvenation by increasing oxygen partial pressure of circulating gas to at least 0.4 atmosphere (39.2 kilopascals (KPa)) and increasing temperature of the catalyst bed to, e.g., 950° F. (510° C.) to 1200° F. 649° C.). Snuggs et al. introduces flue gas produced by combustion of fuel gas to hot compressed air that is passed through the catalyst bed. Rejuvenation times depend upon extent of catalyst deactivation and range from a matter of 5 or 10 minutes for slightly deactivated catalysts to as long as 24 hours for badly deactivated catalysts. Snuggs et al. effects an oxygen purge subsequent to rejuvenation by introducing fuel gas to burn off the oxygen.

British Patent (GB) 735,145 teaches a method for regenerating platinum and/or palladium catalysts that substantially restores their catalytic properties. The method includes treating the platinum and/or palladium catalysts at an elevated temperature (700° F. (371° C.) to 1600° F. (871° C.) with an oxygen-containing gas under such conditions that the oxygen partial pressure is from five pounds per square inch absolute (psia) (34.5 KPa) to 200 psia (1379 KPa). '145 also teaches removal of oxygen associated with catalyst via the proposed treatment by subjecting the catalyst to a hydrogen gas treatment.

In some aspects, this invention is an improved process for dehydrogenating an alkane, the process comprising placing an alkane in operative contact with a heated alkane dehydrogenation catalyst in a reactor, the catalyst comprising a Group VIII noble metal, a Group IIIA metal and, optionally, a promoter metal, removing from the reactor a partially deactivated catalyst, rejuvenating the partially deactivated catalyst in a regenerator, and transporting the rejuvenated catalyst from the regenerator to the reactor, wherein the improvement comprises a combination of treatment within the regenerator and transport of the rejuvenated catalyst from the regenerator to the reactor, the treatment within the regenerator comprising sequential steps:

a. heating the partially deactivated catalyst to a temperature of at least 660 degrees Celsius using heat generated by combusting both coke contained on the partially deactivated catalyst and a fuel source other than said coke, said heating yielding a heated, further deactivated catalyst which has an alkane (e.g. propane) dehydrogenation activity that is less than that of the partially deactivated catalyst;

b. subjecting the heated, further deactivated catalyst to a conditioning step which comprises maintaining the heated, further deactivated dehydrogenation catalyst at a temperature of at least 660 degrees Celsius while exposing the heated, further deactivated dehydrogenation catalyst to a flow of an oxygen-containing gas for a period of time greater than two minutes and sufficient to yield an oxygen-containing reactivated dehydrogenation catalyst that has an activity for dehydrogenating alkane (e.g. propane) that is greater than that of either the partially deactivated catalyst or the further deactivated catalyst; and optionally, but preferably c. maintaining the oxygen-containing reactivated catalyst at a temperature of at least 660 degrees Celsius while exposing the reactivated catalyst to a flow of stripping gas that is substantially free of molecular oxygen and combustible fuel for a period of time sufficient to remove from the oxygen-containing reactivated dehydrogenation catalyst at least a portion of molecular oxygen trapped within or between catalyst particles and physisorbed oxygen that is desorbable at said temperature during that period of time and yield a rejuvenated dehydrogenation catalyst;

with transport from the regenerator to the reactor being effected by a combination of gravity and motive force imparted by an inert transport gas. The rejuvenated dehydrogenation catalyst preferably has substantially the same activity for dehydrogenating propane as the reactivated dehydrogenation catalyst, but a lower activity for forming carbon oxides than the reactivated dehydrogenation catalyst.

While particularly suitable for dehydrogenating propane, the improved process also has utility in dehydrogenating other alkanes, including ethane, butane, and pentane to their respective alkenes (e.g. ethylene when the alkane is ethane). The alkene (e.g. propylene, ethylene or butylene) has utility as a monomer in polymerization processes to produce, for example, polyethylene, polypropylene or an ethylene-propylene copolymer.

Steps a), b) and c) may occur in any apparatus or combination of apparatuses suitable for effecting actions specified in each of such steps. In some embodiments, each of the steps is physically separated from the other two steps, whether by way of barriers or separate vessels. In other embodiments, step a) is physically separated from steps b) and c) or step c) is physically separated from steps a) and b). In such other embodiments, physical separation may occur by using a first apparatus or vessel for one or two of steps a) through c) and a second apparatus or vessel for those of steps a) through c) that do not occur in the first apparatus. Instead of using separate apparatuses, one may interpose physical barriers (e.g. baffles) within a single apparatus to control, minimize or, preferably, eliminate uncontrolled movement of at least one of gases and catalyst in a reverse direction (e.g. from step b) back to step a), a phenomenon sometimes referred to as "backflow" or "back-mixing". Alternately, one may use two apparatuses or vessels, one with a physical barrier and one without a physical barrier. Physical separation also allows one to use a first pressure (e.g. oxygen partial pressure) on one side of the physical separation, whether the separation is effected by a barrier within a single apparatus or by use of two separate apparatuses, and a second pressure, either higher or lower, on the other side of the physical separation.

Steps a) and b), whether physically separated from one another or not, preferably occur in a fluidized bed apparatus that operates in a bubbling, turbulent flow or fast fluid bed mode with a gas superficial velocity sufficient to effect rapid heat and mass transfer. If physically separated, one may independently select any of pressure, temperature, apparatus or operating mode for each of steps a) and b). The gas superficial velocity is desirably a multiple of the minimum velocity needed to effect fluidization of the particles ($V_{mf}$) within the apparatus, preferably at least five times $V_{mf}$, more preferably at least 10 times $V_{mf}$ and still more preferably from 20 times $V_{mf}$ to 100 times $V_{mf}$. In order to minimize solid back mixing between steps a) and b), one may use internal mechanical devices within a fluid bed apparatus such as grids, trays, shed rows, or structured packing. The internal mechanical devices appear to promote contact between flowing gas and catalyst particles while minimizing possible formation of fuel gas or air bubbles of sufficient size to do one or more of creating hot spots, reducing fuel gas conversion or fuel gas combustion efficiency.

Step c) preferably occurs in a fixed, packed, fluidized or moving bed with a flow of oxygen-free gas that is sufficient to effect removal of at least a portion of molecular oxygen trapped within or between catalyst particles and physisorbed oxygen that is desorbable from the catalyst particles at the time and temperature specified above for step c).

The oxygen-containing atmosphere of step b) preferably has an oxygen content within a range of from 5 mol % to 100 mol %, each mol % being based upon total moles of oxygen in the oxygen-containing atmosphere. The oxygen-containing atmosphere is preferably selected from a group consisting of air and molecular oxygen ($O_2$). The oxygen-containing atmosphere may include an amount of steam or water vapor from one or more of combustion zone effluent and moisture contained in the air, as well as an amount nitrogen ($N_2$) such as that normally contained in air.

The period of time for conditioning step b) preferably lies within a range of from at least 2 minutes (min) to no more than 20 min The range is more preferably from 3 min to 14 min The period of time has an inverse relationship to temperature for at least step b) and preferably for both steps a) and b) with a preference for maintaining the temperature below that which leads to an irreversible change in the catalyst. In other words, to reach a desired level of activity for dehydrogenating alkane, one needs a shorter period of time at higher temperatures (e.g. near 750° C.) than one needs at lower temperatures (e.g. near 660° C.). The desired level of activity is a matter of choice, but is greater than that of further deactivated catalyst that exits step a) and less than or equal to that of fresh (previously unused) heated alkane dehydrogenation catalyst prior to the initial operative contact with an alkane in the reactor.

In some embodiments, steps b) and c) are physically separated from one another and an oxygen-containing atmosphere with an oxygen content within a range of from 5 mole percent to 100 mole percent, each mole percent being based upon total moles of oxygen-containing atmosphere, is used to effect catalyst transfer between steps b) and c).

The temperature for steps a), b), and c) is preferably at least 660° C. A practical upper limit on said temperature is 850° C. to avoid challenges such as unwanted side reactions or damage to apparatus components used in conjunction with the process. The temperature more preferably lies within a range of from 660° C. to 780° C., more preferably from 700° C. to 750° C.

Step c) preferably comprises maintaining the heated catalyst at a temperature within the temperature range and exposing the heated catalyst to a flow of oxygen-free gas, preferably an inert gas such as $N_2$, sufficient to remove at least a portion of, more preferably substantially all of residual combustion byproducts and residual oxygen present on the heated catalyst prior to exposure to the flow of oxygen-free gas. "Substantially all" means, in this context, that a heated catalyst subsequent to treatment with the oxygen-free gas preferably has carbon dioxide content of less than 1 wt % and a water content of less than 0.2 wt %, each wt % being based upon total heated catalyst weight.

The oxygen-free gas used in step c) may include small amounts of a carbon oxide, water vapor or both (e.g. no more than two (2) molar percent (mol %) water, no more than 1 mol % carbon dioxide and less than 0.1 mol% carbon monoxide, each mol % being based on total moles of oxygen-free gas), but the oxygen-free gas is preferably substantially free (less than 0.5 mol % water, less than 0.5 mol % carbon dioxide, each mol % being based on total moles of oxygen-free gas, and less than 200 parts by mole per million parts total moles of oxygen-free gas) of carbon oxides and water vapor.

In some embodiments, one may implement an optional precursor step in advance of step a). In such optional precursor step, one subjects the catalyst to a flow of a stripping gas such as steam, methane or nitrogen to remove at least a portion of hydrocarbons contained on the catalyst before subjecting the catalyst to regeneration as provided herein.

An inert gas preferably provides motive force to transport rejuvenated catalyst from the regenerator to the reactor. An inert gas is preferred over an oxygen-containing gas because the latter will react with a reactant gas (an alkane such as propane) to form undesired byproducts such as carbon monoxide, carbon dioxide and possibly an oxygenate. The presence of such byproducts adversely affects process economics. While small amounts of combustion byproducts, such as less than 0.1 mol % of carbon monoxide, less than 1 mol % of carbon dioxide and less than 0.5 mol % of water may be present in an inert gas stream that provides motive force, each mol % being based upon total moles of such inert gas stream, may be tolerated, increasing such amounts leads to a decrease in catalyst performance with small increases leading to small decreases in catalyst performance and larger increases leading to further decreases in catalyst performance. When oxygenates are present, one may also need an additional separation apparatus or facility to recover a desired alkene from a mixture of the alkene and an oxygenate. An inert gas is also preferred over a fuel gas such as hydrogen or methane because fuel gases lead to lower catalyst performance than one obtains with an inert gas.

The catalyst preferably comprises a Group VIII noble metal (e.g. at least one of Pt, Pd, Rh and Ir), a Group IIIA metal (e.g. at least one of gallium (Ga), indium (In), and germanium (Ge)) and, optionally, a promoter metal (e.g. an alkali metal). Group VIII and Group IIIA refer to designations in *The Periodic Table of the Elements* (CAS version). The Group VIII noble metal is preferably platinum, the Group IIIA metal is preferably gallium and the promoter metal is preferably potassium.

The process comprises at least two sequential steps, a heating or combustion step a) and a conditioning step b). In some embodiments, the process also comprises an optional stripping step c) subsequent to step b). The heating or combustion step effects combustion of at least a portion, preferably substantially all, and more preferably all, of coke disposed on surfaces of the partially deactivated dehydrogenation catalyst. The partially deactivated dehydrogenation catalyst has a coke level of, for example, less than 0.3 percent by weight (wt %) based upon total partially deactivated dehydrogenation catalyst weight. The heating or combustion step includes combusting a supplemental fuel source (a fuel other than coke contained on the partially deactivated catalyst) concurrent with combusting or burning the coke disposed on surfaces of the partially deactivated dehydrogenation catalyst. The conditioning step sequentially follows the heating or combustion step and subjects the heated catalyst to treatment with an oxygen-containing gas while maintaining the heated catalyst at an elevated temperature that is preferably at least 660° C., more preferably from 700° C. to 750° C. for a period of time sufficient to increase catalytic activity relative to that of the same catalyst in the absence of the conditioning step. The period of time is at least two (2) minutes, preferably at least three (3) minutes, and more preferably from three (3) minutes to 14 minutes. The oxygen-containing gas is preferably substantially free of combustible hydrocarbons, carbon oxides (especially carbon monoxide and carbon dioxide) and water vapor.

The process converts the partially deactivated dehydrogenation catalyst to a reactivated catalyst that has greater propane dehydrogenation activity than that of the same partially deactivated dehydrogenation catalyst treated with only steps a) heating or combustion and c) stripping.

Each of steps a) and b) and optional step c) can operate in the same fluidization regimes as the other steps or in different gas-solid fluidization regimes or even in a combination of fluidization regimes within each step. These regimes range from minimum fluidization to bubbling fluidization to turbulent bubbling fluidization to circulating fast-fluidization to dilute-phase gas-solid transport regime and incorporating technology known to those in the art to improve fluidization behavior within that fluidization regime, including grids, structured packing, or other internals. Step a) may, for example, occur in a gas-solid counter-flow regenerator operating in the bubbling regime in which solid particles enter from the top of the process and flow downward, exiting at the bottom of a combustion zone while the combusting gas flows upward, or step a) may, for example, occur in a combination of gas-solid co-current flow (i.e. gas and solids flow in a single direction, either upward or downward in a vertical apparatus or vessel). Separately, conditioning step b) may, for example, occur in the same vessel below the step a) and with catalyst entering from the top of the vessel for step b) (exiting from the bottom of the vessel for step a)) and flowing downward, counter-currently to the oxidizing gas flowing upward and maintaining operation in a bubbling regime. Separately, conditioning step b) may occur in a separate zone or vessel and operating in a fluidization regime independent of the fluidization regime in step a), including any fluidization regime from minimum gas-solid fluidization to gas-solid bubbling fluidization to turbulent bubbling fluidization to circulating fast-fluidization to dilute phase gas-solid transport regime. Similarly, optional stripping step c) stripping can occur either as a continuation of the fluidization regime of step b) or operate independently of the fluidization regime in step b).

In some embodiments, physical separation of steps a) and b) from step c) may be effected by use of a device such as an annular stripper. This provides a related benefit in allowing for an increased length to diameter (L/D) ratio within a device, apparatus or vessel used for step b) relative to what one might use in the absence of physical separation (where D is defined as the actual diameter for traditional cylindrical cases and as the annular width for the annular cases). By way of example, conventional fluid catalyst cracking (FCC) bubbling bed regenerators are believed to have L/D ratios that range from 0.1:1 to 1.0:1 for coke combustion. L/D ratios for apparatus used in step c) preferably range from greater than 1.0:1 to 10:1 and more preferably from 2.0:1 to 6.0:1 for those embodiments of the present invention that physically separate steps a) and b) from step c).

In some embodiments, apparatus used for step b) operate with a superficial gas velocity where step b) commences (nominally the "bottom" of the regeneration zone) that ranges between 0.05 feet per second (ft/sec) (0.015 meter per second (m/sec)) to 0.5 ft/sec (0.15 m/sec), more preferably from 0.15 ft/sec (0.046 m/sec) to 0.4 ft/sec (0.0122 m/sec), and still more preferably from 0.2 ft/sec (0.061 m/sec) to 0.3 ft/sec (0.091 m/sec). Catalyst bed density within apparatus used for step b) desirably ranges from 45 pounds per cubic foot ($lb/ft^3$) (720.1 kilograms per cubic meter ($kg/m^3$)) to 70 $lb/ft^3$ (1121.3 $kg/m^3$), preferably from 50 $lb/ft^3$ (800.9 $kg/m^3$) to 65 $lb/ft^3$ (1041.2 $kg/m^3$), and more preferably from 55 $lb/ft^3$ (881.0 $kg/m^3$) to 60 $lb/ft^3$ (961.1 $kg/m^3$).

In some embodiments, apparatus used for step b) operate with a pressure at that end of the apparatus remote from the nominal bottom, nominally the "top" or "top end" of such apparatus, ranging from 10 pounds per square inch absolute (psia) (68.9 kilopascals (kPa) to 60 psia (413.7 kPa)), preferably from 25 psia (172.4 kPa) to 40 psia (275.8 kPa).

In some embodiments, one may recycle at least a portion of catalyst from the apparatus or apparatus portion used for step b) to the apparatus or apparatus portion used for step a). Recycling from the nominal bottom of the apparatus used for step b) may facilitate unit start-up for at least some embodiments of the improved process disclosed herein. Recycling from a nominal top of the apparatus used for step b) (i.e. an end remote from the nominal bottom end) to the apparatus or apparatus portion used for step a) can provide at least some of the catalyst needed for fuel combustion in step a).

In some embodiments, steps b) and c) are physically separated in order to effect step b) at a higher oxygen partial pressure than that used in step c).

"Partially deactivated dehydrogenation catalyst" means a catalyst with a dehydrogenation activity that is greater than 70%, but less than 95%, of the dehydrogenation activity of the same catalyst prior to its use in dehydrogenation, especially PDH (otherwise known as "regenerated" catalyst);, "Further deactivated catalyst" refers to a catalyst that, subsequent to heating step a), has a dehydrogenation activity at least 5% lower than the activity of the partially deactivated dehydrogenation catalyst prior to step a). By way of example, if the partially deactivated dehydrogenation catalyst has a dehydrogenation activity of 90%, the further deactivated catalyst has a dehydrogenation activity of less than 85%.

"Propane dehydrogenation activity" means activity to convert $C_3H_8$ to $C_3H_6$ and hydrogen ($H_2$).

"Substantially free of coke", as applied to a catalyst, refers to a catalyst that has a coke content of less than 0.05 percent by weight (wt %), based upon total catalyst weight.

"Substantially all", when used to describe molecular oxygen and physisorbed oxygen contents of the reactivated catalyst, means that the catalyst has a residual oxygen content of less than 0.1 wt %, based upon total catalyst weight.

The reactivated catalyst also preferably has a combustion product content of less than 1 wt % carbon dioxide ($CO_2$), and less than 0.2 wt % water, in each case based upon catalyst weight as well as less than 100 parts by weight per million parts by weight of catalyst (ppmw) carbon monoxide (CO)

In succeeding paragraphs, Arabic numerals designate examples (Ex) of the invention and capital letters designate comparative examples (CEx).

Conduct experiments at ambient pressure (1 atmosphere (98.1 KPa)) under simulated circulating fluid bed operation conditions in a vertically-oriented, fixed bed quartz reactor. The quartz reactor has a total length, including metal to glass connectors at each end, of 21.75 inches (55.2 centimeters (cm)) and includes a center piece with an outer diameter (O.D.) 0.75 inch (1.9 cm) and a length of two (2) inches (5.1 cm). Insert a coarse frit at the bottom of the center piece to hold particulate catalyst. On each end, the center piece is connected to, and in fluid communication with, a quartz tube that has a length of 6 inches (15.2 cm) and an O.D. of seven (7) millimeters (mm) Fit each distal quartz tube end (remote from the center piece) with a 0.25 inch (0.6 cm) glass to metal connector with a 0.25 inch (0.6 cm) tubing nut that allows one to connect the quartz reactor to a gas injection line and an effluent line. Connect the effluent line, in turn, to a gas chromatograph (GC) and vent. Add a quartz thermo-well to the center piece to allow one to detect temperatures within a catalyst bed. Place two thermocouples inside the thermo-well, one as a heater control and one as a temperature indicator.

For all Ex and CEx, use a supported potassium-platinum-gallium (K—Pt—Ga) catalyst. The catalyst has a metals content of 1.6 percent by weight (wt %) Ga, 0.25 wt % K and 92 parts per million (ppm) Pt, each wt % being based upon total catalyst weight and the ppm being based upon one million parts by weight of total catalyst weight. The support is a silica-modified alumina (SIRALOX™ 5/70, Sasol, 1.5 wt % $SiO_2$ in alumina, surface area of 70 square meters per gram ($m^2/g$)). Premix 0.5 g of the catalyst with 1.0 g silicon carbide (SiC), an inert material having a size of from 200 mesh (74 micrometer (μm) sieve opening) to 450 mesh (26 μm) (Aldrich, Catalog Number 378097) and place the premix on the coarse frit in the center piece of the quartz reactor. Load cylinder-shape quartz chips, an inert material having a height of 2 mm and a diameter of 2 mm (Quartz Scientific Inc.) on top of the premix to fill reactor space within the center piece above the catalyst.

Subject the catalyst to a number of reaction/regeneration cycles as detailed below, each cycle comprising a reaction step and a regeneration step with a stripping step using helium (He) occurring in between the reaction step and the regeneration step. In the reaction step, effect PDH for all examples other than Ex 1 and 2 which have a reaction time of 15 minutes, for 30 seconds (sec) at 600° C. using a feed stream that contains 95 mole percent (mol %) propane ($C_3H_8$) and 5 mol % $N_2$, each mol % being based upon total moles in the feed stream and the $N_2$ serving as an internal standard (ISD). Use a propane weight hourly space velocity (WHSV) of 20 reciprocal hours ($hr^{-1}$). Collect data for propane conversion and $C_3H_6$ selectivity at time zero (that time when 95 mol % of effluent from the reactor is a combination of propane, $N_2$ ISD and propane dehydrogenation products and 5 mol % of the effluent is He left in the reactor system from the stripping step prior to PDH).

After 30 sec, (Examples 3-5 and CEx A-CEx B) or 15 minutes (Ex 1-2 and CEx C and CEx D) under PDH conditions, each time being measured from time zero, ramp reactor temperature to 700° C. at a rate of 20° C. per minute in the presence of a gas stream (specified below) that flows through the reactor at a rate of 120 standard cubic centimeters per minute (sccm).

For regeneration or conditioning, maintain the temperature at 700° C. and use a regeneration gas flow rate of 150 sccm. See Ex and CEx below for regeneration gas composition and duration of the regeneration.

After the regeneration step and before starting another PDH reaction cycle, cool the reactor to the reaction temperature (600° C.) at a rate of 20° C. per minute and let the temperature of the system stabilize over a period of 20 minutes under flowing He (flow rate of 120 sccm) to effect stripping of labile or strippable oxygen from the catalyst, thereby allowing one to introduce propane for dehydrogenation and maintain a propane to oxygen level during PDH below what skilled artisans refer to as a lower explosive limit or LEL As a means of standardizing catalyst activity at a propane conversion of between 40% and 42% between examples, which provide different regeneration conditions, condition the catalyst by running four reaction-regeneration cycles with each regeneration step being conducted at 700° C. for 15 min under 100% air (flow rate 150 sccm). As noted above, effect stripping of labile oxygen before introducing propane for PDH.

EX 1

Evaluate catalyst performance using 100 mol % air as a regenerating gas and a regeneration step time of 15 minutes (min) Effect heating for the reaction step and the regeneration step using a clam-shell furnace. As noted above, use flowing He between the regeneration step and the subsequent reaction step. Table 1 below shows propane conversion percentage and propylene ($C_3H_6$) selectivity percentage after a number of cycles as specified in Table 1.

TABLE 1

| Number Of Cycles | $C_3H_8$ Conversion (%) | $C_3H_6$ Selectivity (%) |
|---|---|---|
| 1 | 41.8 | 99.2 |
| 2 | 42.1 | 99.2 |
| 5 | 41.7 | 99.2 |
| 8 | 41.7 | 99.2 |
| 10 | 42.8 | 99.2 |

The results in Table 1 show that heating in the absence of combustion gases together with a conditioning step using an oxygen-containing gas, in this case air, yields relatively stable catalyst performance in terms of $C_3H_8$ conversion percentage.

EX 2

Replicate Ex 1, but determine $C_3H_8$ conversion % and $C_3H_6$ selectivity % 15 seconds after time zero. Summarize results in Table 2 below.

TABLE 2

| Number Of Cycles | $C_3H_8$ Conversion (%) | $C_3H_6$ Selectivity (%) |
|---|---|---|
| 1 | 35.4 | 99.1 |
| 2 | 37.3 | 99.4 |
| 5 | 38.0 | 99.4 |
| 8 | 37.5 | 99.4 |
| 10 | 37.1 | 99.4 |

The results in Table 2 show that catalyst deactivation occurs to some extent in a relatively short time (15 seconds). Once again, heating in the absence of combustion gases leads to relatively stable catalyst performance.

CEX A

Replicate Ex 1, but change the time under PDH reaction conditions from 15 minutes to 30 seconds, substitute a gaseous mixture of 25 mol % water, 5 mol % oxygen and 70 mol % inert gas (19 mol % $N_2$ and 51 mol % He), each mol % being based upon total moles of gas in the mixture for air, and reduce the regeneration step time to 8 minutes. The gaseous mixture simulates composition of a gas composition within a PDH reactor after combustion of a fuel source and at least a portion of coke contained on the catalyst. Summarize results in Table 3 below.

TABLE 3

| Number Of Cycles | $C_3H_8$ Conversion (%) | $C_3H_6$ Selectivity (%) |
|---|---|---|
| 1 | 40.6 | 99.2 |
| 2 | 37.7 | 99.2 |
| 5 | 35.6 | 99.2 |
| 8 | 34.4 | 99.1 |
| 10 | 33.5 | 99.1 |

The results in Table 3 show that a process that includes only step a) leads to progressively lower catalyst performance results in terms of $C_3H_8$ conversion % and $C_3H_6$ selectivity % as the number of cycles increases.

CEX B

Replicate CEx A, but add a regenerating step c) that is a flow of pure He at a flow rate of 120 sccm for 10 minutes subsequent to the 8 minute regeneration time with the gaseous mixture. Summarize results in Table 4 below.

TABLE 4

| Number Of Cycles | $C_3H_8$ Conversion (%) | $C_3H_6$ Selectivity (%) |
|---|---|---|
| 1 | 41.7 | 99.4 |
| 2 | 38.0 | 99.2 |
| 5 | 35.5 | 99.2 |
| 8 | 33.7 | 99.1 |
| 10 | 33.0 | 99.1 |

The results in Table 4 demonstrate that addition of a step c) to step a) provides no improvement in catalyst performance relative to step a) alone.

EX 3

Replicate CEx B, but introduce a conditioning step b) by adding, subsequent to step a), a two minute flow of 100% air at a rate of 150 sccm. Follow step b) with a flow of He (120 sccm) for 20 minute. Summarize results in Table 5 below.

TABLE 5

| Number Of Cycles | $C_3H_8$ Conversion (%) | $C_3H_6$ Selectivity (%) |
|---|---|---|
| 1 | 41.5 | 99.3 |
| 2 | 37.4 | 99.2 |
| 5 | 35.7 | 99.2 |
| 8 | 34.9 | 99.2 |
| 10 | 34.8 | 99.2 |

The results in Table 5 show that a conditioning step of as little as two minutes leads to some improvement in catalyst performance relative to CEx C and CEx D as the number of cycles reaches 5 cycles.

EX 4

Replicate Ex 3, but change the step b) time to five minutes. Summarize results in Table 6 below.

TABLE 6

| Number Of Cycles | $C_3H_8$ Conversion (%) | $C_3H_6$ Selectivity (%) |
|---|---|---|
| 1 | 41.8 | 99.4 |
| 2 | 38.1 | 99.3 |
| 5 | 37.9 | 99.3 |
| 8 | 37.6 | 99.2 |
| 10 | 37.6 | 99.3 |

EX 5

Replicate Ex 4, but change the step b) time to ten minutes. Summarize results in Table 7 below.

TABLE 7

| Number Of Cycles | $C_3H_8$ Conversion (%) | $C_3H_6$ Selectivity (%) |
|---|---|---|
| 1 | 41.1 | 99.4 |
| 2 | 39.5 | 99.3 |
| 5 | 39.3 | 99.3 |
| 8 | 39.5 | 99.3 |
| 10 | 39.4 | 99.3 |

The results in Tables 6 and 7 show that as the length of conditioning step b) increases, catalyst performance levels out to a relatively steady state, with a longer step b) time of ten minutes providing a relatively steady state performance more rapidly than a step b) time of five minutes and at a higher level of performance once it does reach a relatively steady state.

CEX C and D

Replicate Ex 1, but add a hydrogen gas treatment step using 99.99 percent pure $H_2$ flowing at a rate of 60 sccm for three minutes for CEx C and 15 minutes for CEx D after treatment with flowing He and just prior to the subsequent reaction step. Summarize results in Table 8 below. Table 8 also includes results from Ex 1.

TABLE 8

| Ex/CEx | Number Of Cycles | $C_3H_8$ Conversion (%) | $C_3H_6$ Selectivity (%) |
|---|---|---|---|
| 1 | 1 | 41.8 | 99.2 |
| 1 | 2 | 42.1 | 99.2 |
| C | 1 | 39.0 | 99.2 |
| D | 1 | 30.9 | 98.9 |
| D | 2 | 30.9 | 98.8 |

The data in Table 8 simulate use of a fuel gas as a motive fluid in CEx C and CEx D and show that it adversely affects catalyst performance in terms of $C_3H_8$ conversion relative to using He as a motive fluid.

EX 6 and CEX E

Replicate Ex 1 with several changes. First, change the temperature for catalyst evaluation to 625° C. Second, change the feed stream to 90 mol % $C_3H_8$ and 10 mol % $N_2$, each mol % being based upon combined moles of $C_3H_8$ and $N_2$, and use a reaction time of 60 seconds and a $C_3H_8$ WHSV of 10 hr$^{-1}$. Third, following the reaction time of 60 seconds, heat the catalyst (step a) for three minutes at a temperature of 750° C. with a gaseous mixture of 16 mol % water, 4 mol % oxygen, 8 mol % $CO_2$ and 72 mol % He, each mol % being based upon combined moles of water, oxygen, $CO_2$ and He. Fourth, condition the catalyst (step b.) using air as a regeneration gas for 15 minutes at 750° C. Fifth, cool the reactor from 750° C. to 625° C. and strip oxygen from the catalyst (step c) using flowing He as described above. Sixth, effect 142 reaction/regeneration/cooling cycles before collecting data for Ex 6 as shown in Table 9 below for cycle 143.

For CEx E, change the procedure used for the first 143 cycles by adding an intermediate treatment step between steps b and c wherein the catalyst is subjected to two minutes of flowing (60 sccm) methane ($CH_4$) before collecting data at time zero of cycle 144 as shown in Table 9 below.

TABLE 9

| Ex/CEx | $C_3H_8$ Conversion (%) | $C_3H_6$ Selectivity (%) |
|---|---|---|
| 6 | 46.1 | 96.4 |
| E | 29.3 | 94.1 |

The data in Table 9 demonstrate that exposure to flowing $CH_4$ compromises catalyst activity and leads to further catalyst deactivation as shown by the drop in both $C_3H_8$ conversion and $C_3H_6$ selectivity.

CEX F

Replicate Ex 5, but change the temperature for conditioning from 700° C. to 600° C. and summarize results in Table 10 below.

TABLE 10

| Number Of Cycles | $C_3H_8$ Conversion (%) | $C_3H_6$ Selectivity (%) |
|---|---|---|
| 1 | 41.5 | 99.0 |
| 2 | 38.7 | 99.0 |
| 5 | 37.4 | 99.1 |
| 8 | 36.5 | 99.1 |
| 10 | 35.8 | 99.1 |

The data in Table 10 above demonstrate that, as between a conditioning temperature of 700° C. (Ex 5 and associated Table 7) and a conditioning temperature of 600° C. (CEx F and associated Table 10), the latter temperature leads to a less satisfactory result in terms of a more pronounced reduction in $C_3H_8$ conversion.

CEX G

Replicate Ex 1 with changes. First, change the feed stream to 95 mol % $C_3H_8$ and 5 mol % $N_2$, each mol % being based upon combined moles of $C_3H_8$ and $N_2$, and use a reaction time of 60 seconds and a feed stream weight hourly space velocity of 8 hr$^{-1}$. Second, use a mixture of 25 mol % water ($H_2O$) and 75 mol % air as a regenerating gas and change the regeneration step time from 15 min to 10 min. Third, during stripping over a period of 30 minutes under flowing He (flow rate of 120 sccm), determine relative mol % of $H_2O$ in stripping step effluent by measuring using mass spectroscopy with $H_2O$ content at a time specified in Table 11 below and dividing it by $H_2O$ content at time zero of the stripping step.

TABLE 11

| Time (sec) | Relative Mol % $H_2O$ |
|---|---|
| 0 | 1.0 |
| 15 | 0.09 |
| 59 | 0.01 |
| 240 | 0.003 |
| 1800 | 0.004 |

The data in Table 11 suggest that system water content rapidly drops off during stripping and reaches a baseline after 240 seconds that is consistent within experimental error and is believed to represent a "dry" system. When combined with the data from CEx B, this suggests that simple removal of water is not sufficient to promote recovery of catalyst activity. CEx B provides for an additional six minutes (min)

of stripping (beyond the 4 min (240 seconds (sec)) shown in Table 11, but catalyst activity, in terms of $C_3H_8$ conversion continues to drop as the number of cycles increases.

CEX H

Using the conditions of Ex 1 with a $C_3H_8$ weight hourly space velocity (WHSV) of 20 hr$^{-1}$, a reaction temperature of 625° C., a catalyst platinum (Pt) concentration of 200 parts by weight per million parts by weight (ppm) of catalyst and a reaction time of 15 min, effect $C_3H_8$ dehydrogenation to establish a coke loading on the catalyst. Condition the catalyst as in Ex 1 (100 mol % air at 700° C. for 15 min) and use mass spectrometry to monitor coke combustion via detection of $CO_2$. As shown in Table 12 below, the $CO_2$ concentration (mol %) rapidly peaks (at 15 seconds) then drops off dramatically such that it below the detection limit after 2 minutes.

TABLE 12

| Time (sec) | Mol % $CO_2$ (%) |
|---|---|
| 15 | 0.34 |
| 29 | 0.11 |
| 57 | 0.01 |
| 142 | 0.00 |

The data in Table 12, when combined with the data for Ex 3 and, especially, Ex 4, suggest that simple coke removal is not sufficient to fully restore catalyst activity.

EX 7

Replicate Ex 6 with several changes. First, change the temperature for catalyst evaluation to 620° C. and $C_3H_8$ WHSV to 8 hr$^{-1}$. Second, vary oxygen concentration in the oxygen-containing atmosphere used for step b) as shown in Table 13 below. Third, vary time of treatment with 100% air at those $O_2$ concentrations also as shown in Table 13 below. Fourth, collect $C_3H_8$ conversion data in step a) 30 seconds after starting feed stream flow. Fifth, use a modification of CEx E wherein regeneration is effected in two sequential sub-steps, with sub-step i) exposing the catalyst to a 150 sccm flow of simulated combustion byproducts (4 mol % $O_2$, 8 mol % $CO_2$, 16 mol % $H_2O$ and 72 mol % $N_2$, all mol % being based upon total moles of simulated combustion byproducts) for a period of three minutes followed by sub-step ii) exposing the catalyst to a 150 sccm flow of oxygen-enriched air (see Table 13). Data shown in Table 13 show conversions for the 25$^{th}$ reaction-regeneration cycle (through steps a) through c) of each variation shown in Table 13.

TABLE 13

| | $C_3H_8$ conversion at specified oxygen concentrations in step b) air | | |
|---|---|---|---|
| Time (min) | 21 mol % $O_2$ | 45 mol % $O_2$ | 75 mol % $O_2$ |
| 4 | 45.2 | 46.7 | 48.7 |
| 6 | 46.7 | 48.2 | 50.7 |
| 8 | 48.6 | 51.1 | 52.0 |
| 10 | 49.3 | 50.7 | Not measured |

The data presented in Table 13 demonstrate that increased oxygen concentration in air used for step b) has a beneficial effect upon $C_3H_8$ conversion under the conditions set forth in this Example 7. The data also show that oxygen is involved in the rejuvenating process of recovering catalyst activity Based upon a review of the data presented in Ex 1-7 and CEx A-H, it appears that catalyst activity regeneration or restoration requires a period of exposure to an oxygen-containing atmosphere after the heating or combustion step a). It also appears that oxygen participates in catalyst activity restoration. It further appears that simple $H_2O$ removal and carbon dioxide ($CO_2$) removal are not sufficient to effect catalyst activity restoration.

What is claimed is:

1. An improved process for dehydrogenating an alkane, the process comprising placing an alkane in operative contact with a heated alkane dehydrogenation catalyst in a reactor, the catalyst comprising a Group VIII noble metal and a Group IIIA metal, removing from the reactor a partially deactivated catalyst, rejuvenating the partially deactivated catalyst in a regenerator, and transporting the rejuvenated catalyst from the regenerator to the reactor, wherein the improvement comprises a combination of treatment within the regenerator and transport of the rejuvenated catalyst from the regenerator to the reactor, the treatment within the regenerator comprising sequential steps:

a. heating the partially deactivated catalyst to a temperature of at least 660 degrees Celsius using heat generated by combusting both coke contained on the partially deactivated catalyst and a fuel source other than said coke, said heating yielding a heated, further deactivated catalyst which has an alkane dehydrogenation activity that is less than that of the partially deactivated catalyst wherein combusting the fuel source other than said coke occurs concurrent with combusting said coke contained on the partially deactivated catalyst;

b. subjecting the heated, further deactivated catalyst to a conditioning step which comprises maintaining the heated, further deactivated dehydrogenation catalyst at a temperature of at least 660 degrees Celsius while exposing the heated, further deactivated dehydrogenation catalyst to a flow of an oxygen-containing gas for a period of time greater than two minutes to yield an oxygen-containing reactivated dehydrogenation catalyst that has an activity for dehydrogenating alkane that is greater than that of either the partially deactivated catalyst or the further deactivated catalyst; and, optionally, c. maintaining the oxygen-containing reactivated catalyst at a temperature of at least 660 degrees Celsius while exposing the reactivated catalyst to a flow of stripping gas that is substantially free of molecular oxygen and combustible fuel for a period of time to remove from the oxygen-containing reactivated dehydrogenation catalyst at least a portion of molecular oxygen trapped within or between catalyst particles and physisorbed oxygen that is desorbable at said temperature during that period of time and yield a rejuvenated dehydrogenation catalyst; with transport from the regenerator to the reactor being effected by a combination of gravity and motive force imparted by an inert transport gas.

2. The process of claim 1, wherein the oxygen-containing gas has an oxygen content within a range of from 5 mole percent to 100 mole percent, each mole percent being based upon total moles of oxygen-containing gas.

3. The process of claim 1, wherein the period of time in step b is within a range of from at least three minutes to no more than 14 minutes.

4. The process of claim 1, wherein the temperature for step b lies within a range of from 660 degrees Celsius to 850 degrees Celsius.

5. The process of claim 1, wherein the partially deactivated catalyst comprises a Group VIII noble metal, and a Group IIIA metal, wherein the Group VIII noble metal is platinum and the Group IIIA metal is gallium.

6. The process of claim 1, wherein one or more of steps a), b) and c) are physically separated from one another.

7. The process of claim 6, wherein steps b) and c) are physically separated from one another and an oxygen-containing atmosphere with an oxygen content within a range of from 5 mole percent to 100 mole percent, each mole percent being based upon total moles of oxygen-containing atmosphere, is used to effect catalyst transfer between steps b) and c).

8. The process of claim 1, wherein the partially deactivated catalyst comprises a promoter metal.

* * * * *